(12) United States Patent
Stearns et al.

(10) Patent No.: US 9,907,569 B2
(45) Date of Patent: Mar. 6, 2018

(54) TROCAR ASSEMBLY WITH PNEUMATIC SEALING

(71) Applicant: SurgiQuest, Inc., Milford, CT (US)

(72) Inventors: Ralph Stearns, Bozrah, CT (US); Raymond Yue-Sing Tang, Rosemead, CA (US); Dominick Mastri, Bridgeport, CT (US)

(73) Assignee: Conmed Corporation, Utica, NY (US)

( * ) Notice: Subject to any disclaimer, the term of this patent is extended or adjusted under 35 U.S.C. 154(b) by 847 days.

(21) Appl. No.: 14/329,364

(22) Filed: Jul. 11, 2014

(65) Prior Publication Data
US 2015/0025323 A1   Jan. 22, 2015

Related U.S. Application Data

(63) Continuation of application No. 13/414,186, filed on Mar. 7, 2012, now Pat. No. 8,795,223.
(Continued)

(51) Int. Cl.
*A61B 17/34* (2006.01)
*A61B 17/00* (2006.01)

(52) U.S. Cl.
CPC ...... *A61B 17/3423* (2013.01); *A61B 17/3462* (2013.01); *A61B 17/3474* (2013.01);
(Continued)

(58) Field of Classification Search
CPC ............ A61B 14/3423; A61B 14/3462; A61B 14/3474; A61B 14/3445
See application file for complete search history.

(56) References Cited

U.S. PATENT DOCUMENTS

| 3,224,320 A | 12/1965 | Knudsen |
| 3,357,433 A | 12/1967 | Fourestier et al. |

(Continued)

FOREIGN PATENT DOCUMENTS

| DE | 2538758 A1 | 3/1977 |
| DE | 2847561 A1 | 5/1980 |

(Continued)

OTHER PUBLICATIONS

International Search Report and Written Opinion for PCT/US2012/28065, dated Aug. 28, 2012.
(Continued)

*Primary Examiner* — Laura Bouchelle
(74) *Attorney, Agent, or Firm* — Locke Lord LLP; Scott D. Wofsy

(57) ABSTRACT

A trocar assembly for creating a pneumatic seal during a minimally-invasive surgical procedure. The trocar assembly including an elongated body having a lumen extending therethrough. The proximal end portion of the body defining a housing. A fluid supply plenum is defined in the housing configured to deliver pressurized insufflation fluid to a nozzle. The nozzle configured for directing pressurized fluid into the lumen and creating a pneumatic seal. A fluid return plenum is defined in the housing configured to collect spent insufflation fluid from as patient's abdominal cavity. The fluid return plenum including a plurality of axially and radially oriented elongate vanes configured to permit spent insufflation fluid to proceed between the vanes and direct spent insufflation fluid back to the fluid return plenum.

8 Claims, 16 Drawing Sheets

Related U.S. Application Data

(60) Provisional application No. 61/450,281, filed on Mar. 8, 2011.

(52) U.S. Cl.
CPC .............. *A61B 2017/00477* (2013.01); *A61B 2017/3445* (2013.01); *A61B 2217/007* (2013.01)

(56) References Cited

U.S. PATENT DOCUMENTS

| | | | |
|---|---|---|---|
| 3,459,189 A | 8/1969 | Alley et al. |
| 3,556,085 A | 1/1971 | Takahashi |
| 4,184,510 A | 1/1980 | Murry et al. |
| 4,191,191 A | 3/1980 | Auburn |
| 4,265,572 A | 5/1981 | Bourdois et al. |
| 4,319,563 A | 3/1982 | Kubota |
| 4,535,773 A | 8/1985 | Yoon |
| 4,735,603 A | 4/1988 | Goodson et al. |
| 4,792,335 A | 12/1988 | Goosen et al. |
| 4,869,717 A | 9/1989 | Adair |
| 5,013,294 A | 5/1991 | Baier |
| 5,057,082 A | 10/1991 | Burchette, Jr. |
| 5,058,603 A | 10/1991 | Doi et al. |
| 5,066,288 A | 11/1991 | Deniega et al. |
| 5,122,122 A | 6/1992 | Allgood |
| 5,147,376 A | 9/1992 | Pianetti et al. |
| 5,159,920 A | 11/1992 | Condon et al. |
| 5,190,068 A | 3/1993 | Philbin |
| 5,199,944 A | 4/1993 | Cosmescu |
| 5,203,767 A | 4/1993 | Cloyd |
| 5,256,149 A | 10/1993 | Banik et al. |
| 5,271,380 A | 12/1993 | Riek et al. |
| 5,284,473 A | 2/1994 | Calabria |
| 5,290,276 A | 3/1994 | Sewell, Jr. |
| 5,300,047 A | 4/1994 | Beurrier |
| 5,312,351 A | 5/1994 | Gerrone |
| 5,328,458 A | 7/1994 | Sekino et al. |
| 5,330,437 A | 7/1994 | Durman |
| 5,334,150 A | 8/1994 | Kaali |
| 5,342,383 A | 8/1994 | Thomas |
| 5,376,076 A | 12/1994 | Kaali |
| 5,380,291 A | 1/1995 | Kaali |
| 5,385,572 A | 1/1995 | Nobles et al. |
| 5,391,153 A | 2/1995 | Haber et al. |
| 5,405,328 A | 4/1995 | Vidal et al. |
| 5,429,483 A | 7/1995 | Tamari |
| 5,431,151 A | 7/1995 | Riek et al. |
| 5,441,041 A | 8/1995 | Sauer et al. |
| 5,445,142 A | 8/1995 | Hassler, Jr. |
| 5,467,762 A | 11/1995 | Sauer et al. |
| 5,545,150 A | 8/1996 | Danks et al. |
| 5,551,947 A | 9/1996 | Kaali |
| 5,556,386 A | 9/1996 | Todd |
| 5,562,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger et al. |
| 5,591,192 A | 1/1997 | Privitera et al. |
| 5,607,440 A | 3/1997 | Danks et al. |
| 5,607,441 A | 3/1997 | Sierocuk et al. |
| 5,609,562 A | 3/1997 | Kaali |
| 5,624,459 A | 4/1997 | Kortenbach et al. |
| 5,647,840 A | 7/1997 | D'Amelio et al. |
| 5,658,236 A | 8/1997 | Sauer et al. |
| 5,674,184 A | 10/1997 | Hassler, Jr. |
| 5,685,820 A | 11/1997 | Riek et al. |
| 5,690,664 A | 11/1997 | Sauer et al. |
| 5,697,913 A | 12/1997 | Sierocuk et al. |
| 5,707,382 A | 1/1998 | Sierocuk et al. |
| 5,720,761 A | 2/1998 | Kaali |
| 5,738,628 A | 4/1998 | Sierocuk et al. |
| 5,779,728 A | 7/1998 | Lunsford et al. |
| 5,797,943 A | 8/1998 | Danks et al. |
| 5,797,944 A | 8/1998 | Nobles et al. |
| 5,800,381 A | 9/1998 | Ognier |
| 5,800,451 A | 9/1998 | Buess et al. |
| 5,817,061 A | 10/1998 | Goodwin et al. |
| 5,817,062 A | 10/1998 | Flom et al. |
| 5,849,005 A | 12/1998 | Garrison et al. |
| 5,860,996 A | 1/1999 | Urban et al. |
| 5,916,198 A | 6/1999 | Dillow |
| 5,951,464 A | 9/1999 | Takahashi et al. |
| 5,976,168 A | 11/1999 | Chin |
| 5,989,228 A | 11/1999 | Danks et al. |
| 6,007,481 A | 12/1999 | Riek et al. |
| 6,017,356 A | 1/2000 | Frederick et al. |
| 6,030,402 A | 2/2000 | Thompson et al. |
| 6,042,573 A | 3/2000 | Lucey |
| 6,056,766 A | 5/2000 | Thompson et al. |
| 6,063,099 A | 5/2000 | Danks et al. |
| 6,162,196 A | 12/2000 | Hart et al. |
| 6,203,568 B1 | 3/2001 | Lombardi et al. |
| 6,206,823 B1 | 3/2001 | Kolata et al. |
| 6,217,555 B1 | 4/2001 | Hart et al. |
| 6,228,058 B1 | 5/2001 | Dennis et al. |
| D443,360 S | 6/2001 | Haberland |
| 6,253,766 B1 | 7/2001 | Niles et al. |
| 6,277,137 B1 | 8/2001 | Chin |
| 6,283,948 B1 | 9/2001 | McKernan et al. |
| 6,299,592 B1 | 10/2001 | Zander |
| 6,302,873 B1 | 10/2001 | Moenning |
| 6,309,382 B1 | 10/2001 | Garrison et al. |
| 6,439,541 B1 | 8/2002 | Nosel et al. |
| 6,447,527 B1 | 9/2002 | Thompson et al. |
| 6,471,638 B1 | 10/2002 | Chang et al. |
| 6,478,806 B2 | 11/2002 | McFarlane |
| 6,482,181 B1 | 11/2002 | Racenet et al. |
| 6,497,687 B1 | 12/2002 | Blanco |
| 6,508,859 B1 | 1/2003 | Zia et al. |
| 6,544,210 B1 | 4/2003 | Trudel et al. |
| 6,579,270 B2 | 6/2003 | Sussman et al. |
| 6,613,063 B1 | 9/2003 | Hunsberger |
| 6,645,197 B2 | 11/2003 | Garrison et al. |
| 6,685,630 B2 | 2/2004 | Sauer et al. |
| 6,685,665 B2 | 2/2004 | Booth et al. |
| 6,692,467 B2 | 2/2004 | McFarlane |
| 6,830,578 B2 | 12/2004 | O'Heeron et al. |
| 6,835,201 B2 | 12/2004 | O'Heeron et al. |
| 6,863,674 B2 | 3/2005 | Kasahara et al. |
| 6,884,253 B1 | 4/2005 | McFarlane |
| 6,905,489 B2 | 6/2005 | Mantell et al. |
| 6,908,454 B2 | 6/2005 | McFarlane |
| 6,918,871 B2 | 7/2005 | Schulze |
| 6,939,296 B2 | 9/2005 | Ewers et al. |
| 6,942,671 B1 | 9/2005 | Smith |
| 6,960,164 B2 | 11/2005 | O'Heeron |
| 7,182,752 B2 | 2/2007 | Stubbs et al. |
| 7,285,112 B2 | 10/2007 | Stubbs et al. |
| 7,297,141 B2 | 11/2007 | Kathrani et al. |
| 7,338,473 B2 | 3/2008 | Campbell et al. |
| 7,413,559 B2 | 8/2008 | Stubbs et al. |
| 7,563,250 B2 | 7/2009 | Wenchell |
| 7,798,998 B2 | 9/2010 | Thompson et al. |
| 7,806,870 B2 | 10/2010 | Mastri et al. |
| 7,854,724 B2 | 12/2010 | Stearns et al. |
| 7,976,598 B2 | 7/2011 | Matula et al. |
| 8,075,481 B2 | 12/2011 | Park et al. |
| 8,088,189 B2 | 1/2012 | Matula et al. |
| 8,114,018 B2 | 2/2012 | Park et al. |
| D663,838 S | 7/2012 | Mastri et al. |
| 8,216,189 B2 | 7/2012 | Stubbs et al. |
| D667,954 S | 9/2012 | Mastri et al. |
| 8,317,815 B2 | 11/2012 | Mastri et al. |
| 8,715,219 B2 | 5/2014 | Stearns et al. |
| RE44,972 E | 7/2014 | Matula et al. |
| 8,795,223 B2 | 8/2014 | Stearns et al. |
| 8,795,235 B2 | 8/2014 | Mastri et al. |
| 2002/0013597 A1 | 1/2002 | McFarlane |
| 2002/0120226 A1 | 8/2002 | Beck |
| 2002/0128603 A1 | 9/2002 | Booth et al. |
| 2002/0143236 A1 | 10/2002 | Sauer et al. |
| 2002/0161387 A1 | 10/2002 | Blanco |

(56) References Cited

U.S. PATENT DOCUMENTS

| | | |
|---|---|---|
| 2003/0040711 A1 | 2/2003 | Racenet et al. |
| 2003/0045834 A1 | 3/2003 | Wing et al. |
| 2004/0034339 A1 | 2/2004 | Stoller et al. |
| 2004/0158126 A1 | 8/2004 | Sauer et al. |
| 2004/0199121 A1 | 10/2004 | Wenchell et al. |
| 2004/0204671 A1 | 10/2004 | Stubbs et al. |
| 2005/0004512 A1 | 1/2005 | Campbell et al. |
| 2005/0010164 A1 | 1/2005 | Mantell |
| 2005/0015043 A1 | 1/2005 | Stubbs et al. |
| 2005/0075605 A1 | 4/2005 | Lyon |
| 2005/0107815 A1 | 5/2005 | McFarlane |
| 2005/0107816 A1 | 5/2005 | Pingleton et al. |
| 2005/0251190 A1 | 11/2005 | McFarlane |
| 2005/0261717 A1 | 11/2005 | Sauer et al. |
| 2006/0079925 A1 | 4/2006 | Kerr |
| 2006/0182637 A1 | 8/2006 | Jacobsen et al. |
| 2007/0088275 A1 | 4/2007 | Stearns et al. |
| 2008/0086160 A1 | 4/2008 | Mastri et al. |
| 2008/0262302 A1 | 10/2008 | Azarbarzin et al. |
| 2009/0137943 A1 | 5/2009 | Stearns et al. |
| 2010/0185057 A1 | 7/2010 | Stearns et al. |
| 2010/0185139 A1* | 7/2010 | Stearns ............. A61B 17/3474 604/26 |
| 2011/0125084 A1 | 5/2011 | Stearns et al. |
| 2012/0010569 A1* | 1/2012 | Parihar ............. A61B 17/3421 604/167.01 |
| 2012/0138523 A1 | 6/2012 | Matula et al. |
| 2012/0150101 A1 | 6/2012 | Stearns et al. |
| 2013/0012782 A1 | 1/2013 | Stearns et al. |
| 2013/0060091 A1 | 3/2013 | Azarbarzin et al. |
| 2013/0231606 A1 | 9/2013 | Stearns et al. |
| 2014/0025047 A1 | 1/2014 | Azarbarzin et al. |
| 2014/0074015 A1 | 3/2014 | Mastri et al. |
| 2014/0088491 A1 | 3/2014 | Azarbarzin et al. |
| 2014/0171855 A1 | 6/2014 | Mastri et al. |
| 2014/0188038 A1 | 7/2014 | Stearns et al. |
| 2014/0309583 A1 | 10/2014 | Stearns et al. |
| 2014/0323807 A1 | 10/2014 | Mastri et al. |
| 2014/0336567 A1 | 11/2014 | Stearns et al. |
| 2014/0358070 A1 | 12/2014 | Sterns et al. |

FOREIGN PATENT DOCUMENTS

| | | |
|---|---|---|
| DE | 4133073 A1 | 4/1992 |
| DE | 19523685 A1 | 1/1997 |
| EP | 0484725 B1 | 5/1992 |
| EP | 0323018 B1 | 6/1993 |
| EP | 0577400 B1 | 1/1994 |
| EP | 0664992 B1 | 8/1995 |
| EP | 1188415 A3 | 5/2002 |
| EP | 1685792 A1 | 8/2006 |
| EP | 1707132 B1 | 10/2006 |
| GB | 2173312 A | 10/1986 |
| WO | WO-9411040 A1 | 5/1994 |
| WO | WO-199601132 A1 | 1/1996 |
| WO | WO-1998/19736 A1 | 5/1998 |
| WO | WO-2000/37134 A1 | 6/2000 |
| WO | WO-2001/91653 A3 | 5/2002 |
| WO | WO-2002085444 A1 | 10/2002 |
| WO | WO-2002/33108 A3 | 10/2003 |
| WO | WO-2010082722 A1 | 7/2010 |

OTHER PUBLICATIONS

"Infant Flow System" from www.eme-med.co.uk.
"Air Jets and Nozzles" from www.exair.com.
Annex to Form PCT/ISA/206—Communication Relating to the Results of the Partial International Search in connection with PCT/US2006/045961 dated Jun. 15, 2007.
International Search Report issued in PCT Application No. PCT/US2007/088017, dated Mar. 9, 2009.
International Search Report and Written Opinion issued for PCT/US2007/021387 dated Jul. 30, 2008.
Office Action for European Patent Application No. 07839288.3 dated Nov. 10, 2011.
International Search Report for PCT/US2011/032305 dated May 24, 2011.
Written Opinion for PCT/US2011/032305 dated Oct. 13, 2012.
Written Opinion for PCT/US2007/088017 dated Jun. 18, 2009.
Office Action for Japanese patent Application No. 2009-527335, dated Jan. 24, 2012.
Decision of Refusal for Japanese patent Application No. 2009-527335, dated Dec. 18, 2012.
Extended European Search Report for European Patent Application No. 11152046.6, dated Apr. 12, 2011.
European Patent Office Communication for European Patent Application No. 06838756.2, dated Jul. 30, 2009.
Office Action for European Patent Application No. 07839288.3 dated Nov. 21, 2012.
Notification of Reasons for Refusal for Japanese Patent Application No. 2009-527335 dated Jan. 21, 2014.
Invitation to Written Reply for Japanese Patent Application No. 2009-527335 dated Jun. 17, 2013.

\* cited by examiner

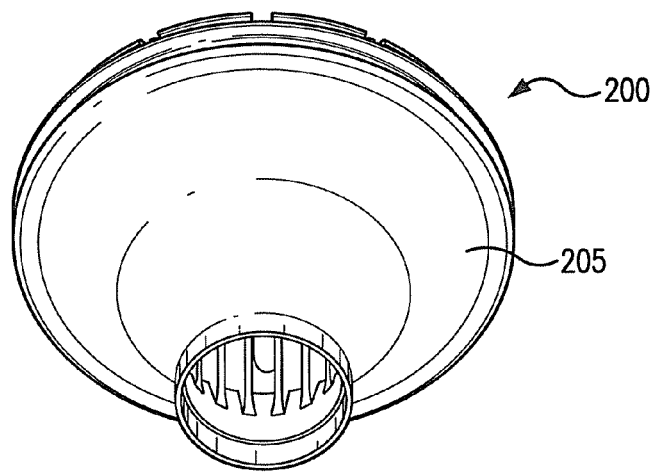
FIG. 21A
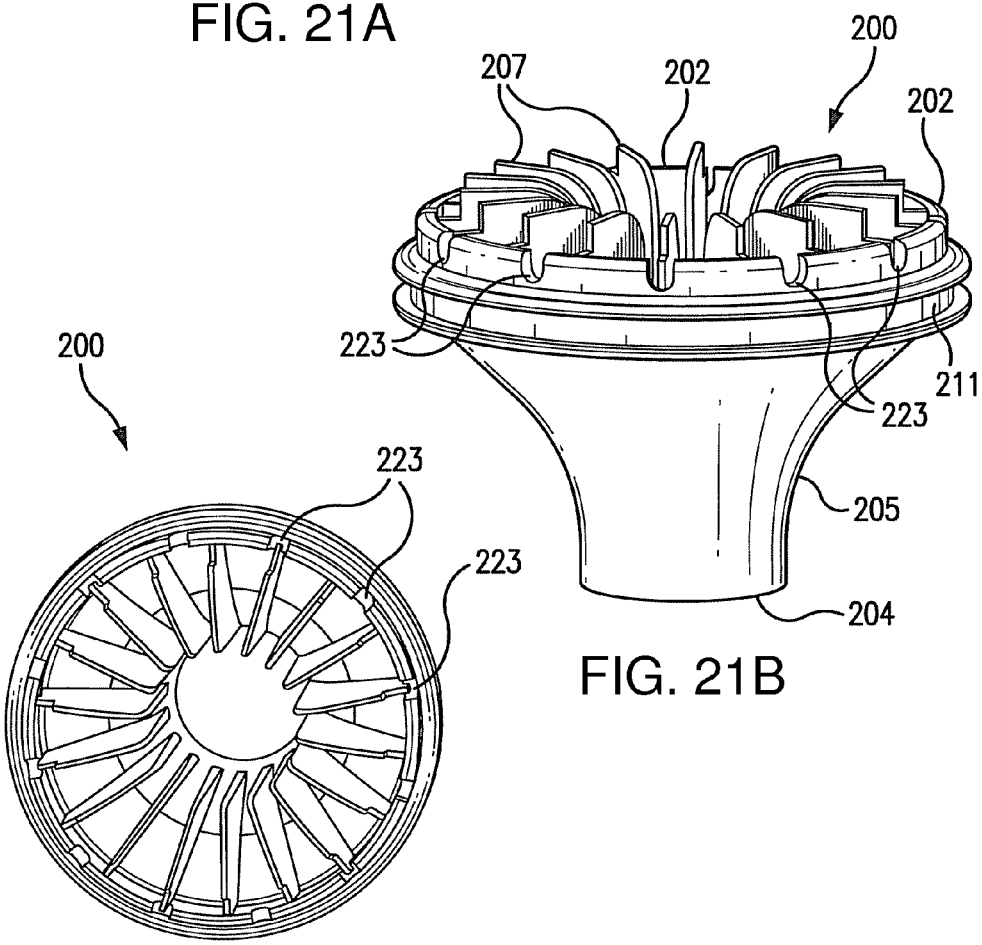
FIG. 21B
FIG. 21C

TROCAR ASSEMBLY WITH PNEUMATIC SEALING

CROSS-REFERENCE TO RELATED APPLICATIONS

This application is a continuation of U.S. patent application Ser. No. 13/414,186, filed Mar. 7, 2012 which claims priority to U.S. patent application Ser. No. 61/450,281, filed Mar. 8, 2011, which is incorporated herein by reference in its entirety. This patent application is also related to U.S. Pat. No. 7,854,724, filed Sep. 8, 2006, U.S. patent application Ser. No. 12/577,179, filed Oct. 10, 2009, U.S. patent application Ser. No. 12/577,189, filed Oct. 11, 2009, U.S. patent application Ser. No. 12/587,584, filed Oct. 9, 2009, U.S. Provisional Patent Application Ser. No. 61/250,521, filed Oct. 11, 2009, U.S. patent application Ser. No. 11/786,832, filed Apr. 13, 2007, U.S. patent application Ser. No. 11/544,856, filed Oct. 6, 2006 and U.S. patent application Ser. No. 61/104,501, filed Oct. 10, 2008. Each of the aforementioned patent applications is incorporated by reference herein in its entirety.

FIELD OF THE INVENTION

The present disclosure relates to surgical access devices (or surgical access ports) and is particularly directed to devices adapted and configured to create a fluidic (pneumatic).

BACKGROUND OF THE INVENTION

The present application relates devices for surgical access, and is particularly directed devices adapted and configured to create a fluidic seal. Surgical access devices configured for creating a fluidic seal for surgical access are set forth in the following applications, which are incorporated herein by reference in their entirety: U.S. Pat. No. 7,854,724, U.S. patent application Ser. No. 11/517,929, filed Sep. 8, 2006, U.S. patent application Ser. No. 10/776,923, filed Feb. 11, 2004, U.S. patent application Ser. No. 10/739,872, filed Dec. 18, 2003, U.S. patent application Ser. No. 10/441,149, filed May 17, 2003, and U.S. Provisional Application Ser. No. 60/461,149, filed Apr. 8, 2003.

Laparoscopic, or "minimally invasive" surgical techniques are becoming increasingly more common. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable, in order to maintain the pneumoperitoneum. During typical laparoscopic procedures, a surgeon makes three to four small incisions, usually no larger than about twelve millimeters each, which are typically made with the trocar devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar. However, sealing in this manner is not usually complete, such seals cannot seal between multiple instruments, and such seals also inhibit free movement of the surgical instruments and/or removal of tissue through the trocar. Such seals are also vulnerable to damage during the surgical procedure. Alternatively, a flapper valve or spring-loaded trap door can be used. However, these types of mechanical valves suffer from similar drawbacks. Most valves, and particularly duckbill-type valves, which include resilient valve members that directly contact surgical instruments, not only interfere with the movement of surgical instruments, but reduce the ability of a surgeon to accurately sense the patient anatomy on which the surgeon is operating. Minimally invasive surgical procedures are carried out with a visualization aid such as a camera, and as a result, depth perception on the part of the surgeon is inhibited. Moreover, when the endoscope passes through mechanical seals, lenses thereof can be dirtied, typically with smears appearing, resulting in further vision difficulty. The absence of mechanical seals also allows swabs and specimens to be extracted without excessive interference. Additionally, the ability to physically sense resistance of structures and of tissues through movement of the surgical instruments plays an important role in a successful and safe surgical procedure. Frictional forces imparted on surgical instruments by contact of the aforementioned mechanical valves can mask the sensory signals, i.e., the haptic perception, that the surgeon might otherwise use to determine precisely what is occurring at the opposite end of the surgical instruments being used. Accordingly, improvements to sealing technologies that allow unencumbered access while maintaining a pneumoperitoneum, are desired. The present invention provides a solution for these problems.

SUMMARY OF THE INVENTION

The purpose and advantages of the invention will be set forth in and apparent from the description that follows. Additional advantages of the invention will be realized and attained by the devices, systems and methods particularly pointed out in the written description and claims hereof, as well as from the appended drawings.

To achieve these and other advantages and in accordance with the purpose of the invention, as embodied, the invention includes, in one embodiment, a trocar for use in a minimally-invasive surgical procedure. In one illustrated embodiment, the trocar includes an elongated body having a proximal end portion which defines a housing. The trocar further includes a first insert having a substantially tubular configuration extending through the elongated body. A second insert is arranged in the housing proximal the first insert. The second insert has a substantially annular configuration and a plurality of axially and radially oriented elongate vanes, each permitting spent insufflation fluid to proceed between the vanes for allowing passage of spent insufflation fluid to pass therethrough. A third insert is arranged in the housing proximal the second insert. The third insert has a substantially annular configuration, wherein the housing, first, second and third inserts define respective walls of a fluid return plenum. The fluid return plenum configured to collect spent insufflation fluid A fourth insert arranged in the housing, preferably proximal to the third insert. The fourth insert has preferably has a substantially annular configuration and substantially tubular member extending distally therefrom. A nozzle is defined on the fourth insert between the substantially tubular member and an central portion of the third insert wherein a locking assembly is provided for nesting, and temporarily locking, the third insert at a spaced distance from the fourth insert. The housing, third and fourth inserts define a fluid supply plenum in fluid communication with the nozzle configured for creating a pneumatic seal.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 10B is a side view of the tube center assembly, wherein FIGS. 10A and 10B present side views at two different angular perspectives of rotation around a central longitudinal axis of the device of FIG. 1;

FIG. 21A is a perspective view of the proximal portion of the inner cannula from a distal vantage point;

FIG. 21B is a perspective view of the proximal portion of the inner cannula from a lateral vantage point;

FIG. 21C is a perspective view of the proximal portion of the inner cannula from a proximal vantage point;

WRITTEN DESCRIPTION OF CERTAIN EMBODIMENTS OF THE INVENTION

Figure 1:
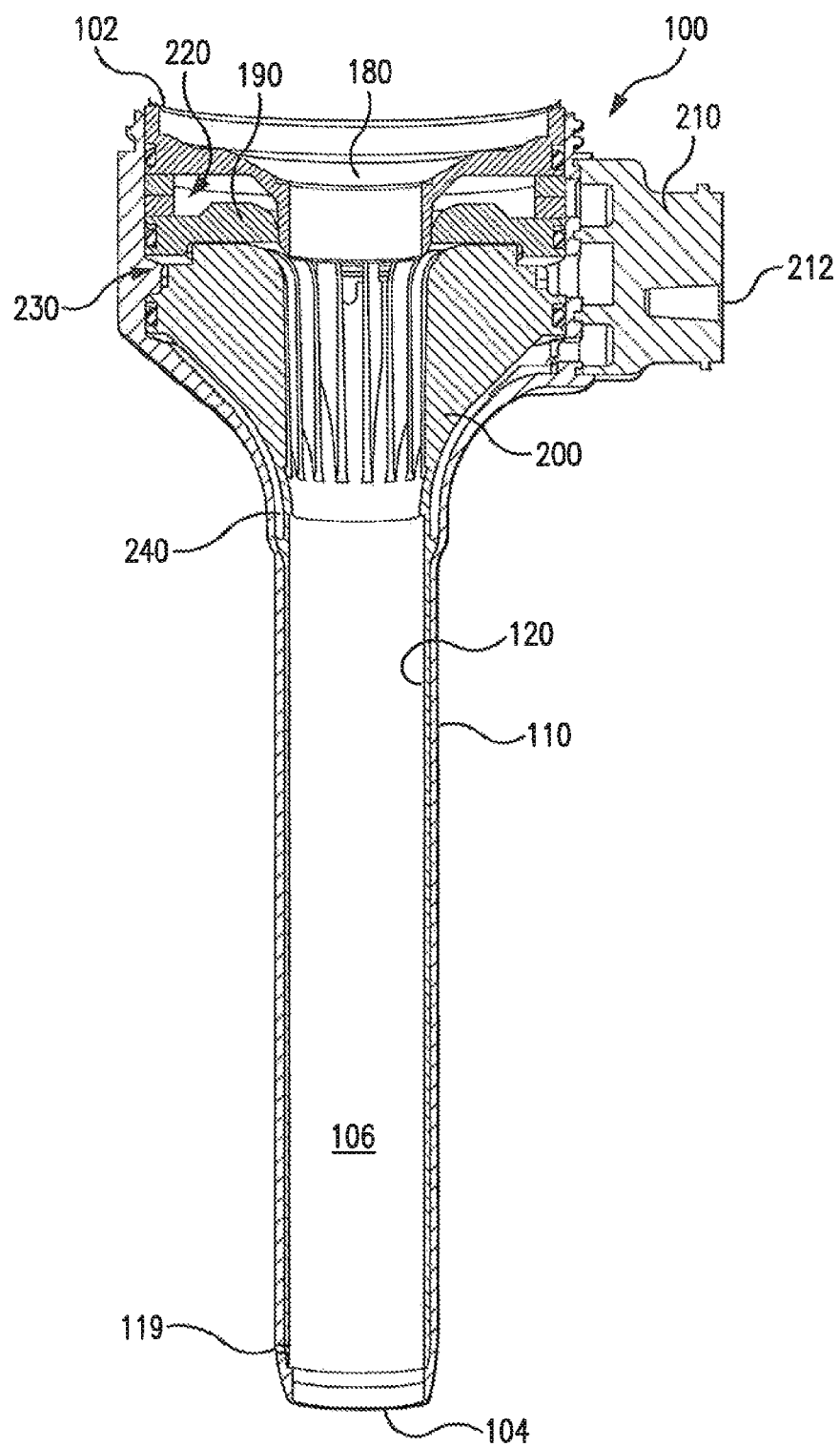
FIG. 1 is a cross sectional view of a portion of an exemplary trocar in accordance with the invention.

The present invention is now described more fully with reference to the accompanying drawings, in which an illustrated embodiment of the present invention is shown. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or systems/devices in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

As set forth above, Applicant has developed a series of trocars that do not use typical mechanical seals to maintain a pressure differential between the operating room and an insufflated abdominal cavity. These trocars generally depend instead on the momentum of a high speed gas stream to counteract gas attempting to escape from the abdomen. Examples of such trocars can be found in the patent applications incorporated by reference on the first page of this patent application as well as those disclosed in U.S. Pat. No. 7,182,752, U.S. Pat. No. 7,285,112, U.S. Pat. No. 7,338,473 and U.S. Pat. No. 7,413,559, which are also incorporated by reference herein in their entireties. Such trocars do not use a mechanical seal to prevent the escape of insufflation gas or body fluids or effluents from the insufflated abdominal cavity of a patient. As a result, multiple surgical instruments of differing cross sections can be used alone, or simultaneously, to perform any number of procedures. The present disclosure relates to improvements in such systems.

By way of introduction, a portion of an exemplary trocar is provided and illustrated in FIGS. 1-21. As embodied herein and as illustrated in FIG. 1, trocar 100 (shown in cross-sectional view) includes a proximal end 102, a distal end 104 and a substantially cylindrical bore 106 therethrough from the proximal end 102 to the distal end 104. Bore 106 (also known as a lumen) is preferably sized and adapted to receive one or more instruments therethrough.

As further illustrated in FIG. 1, trocar 100 is made by assembling a number of nested components discussed in further detail below. As depicted in FIG. 1, trocar 100 includes, in a nested configuration, an outer cannula 110, an inner cannula 120, a tube center component 180 and a ring jet assembly 190. Inner cannula 120 includes a proximal vaned section 200. Trocar 100 further includes a fluid manifold 210 attached to an exterior portion of the outer cannula 110. Each of the aforementioned components will now be illustrated in further detail. The configuration of trocar 100 is generally similar to those incorporated by reference herein, but with some notable differences. These differences principally rely in the configuration of the tube center component 180, the ring jet assembly 190 and the proximal portion 200 of inner cannula 120.

As illustrated, fluid manifold 210 defines therethrough three fluid passages that initiate at ports 212 on the side of manifold 210 and that form passages that pass through the side of outer cannula 110. Each of the aforementioned fluid passages cooperate with the other portions of trocar 110 to define fluid passages, or plena. Each plenum, annotated by reference numerals 220, 230 and 240, serves a different purpose in operation of trocar 100 as described below. Manifold 210 is preferably permanently joined to outer cannula 110 to ensure that the fluid plena remain fluidly separated from each other by way of a gas tight seal. Outer cannula 110 further defines a plurality of sensing ports 119 therethrough. When assembled with other trocar components, sensing ports 119 are in fluid communication with a sensing plenum 240 defined by, inter alia, outer cannula 110 and inner cannula 120.

Figure 2:
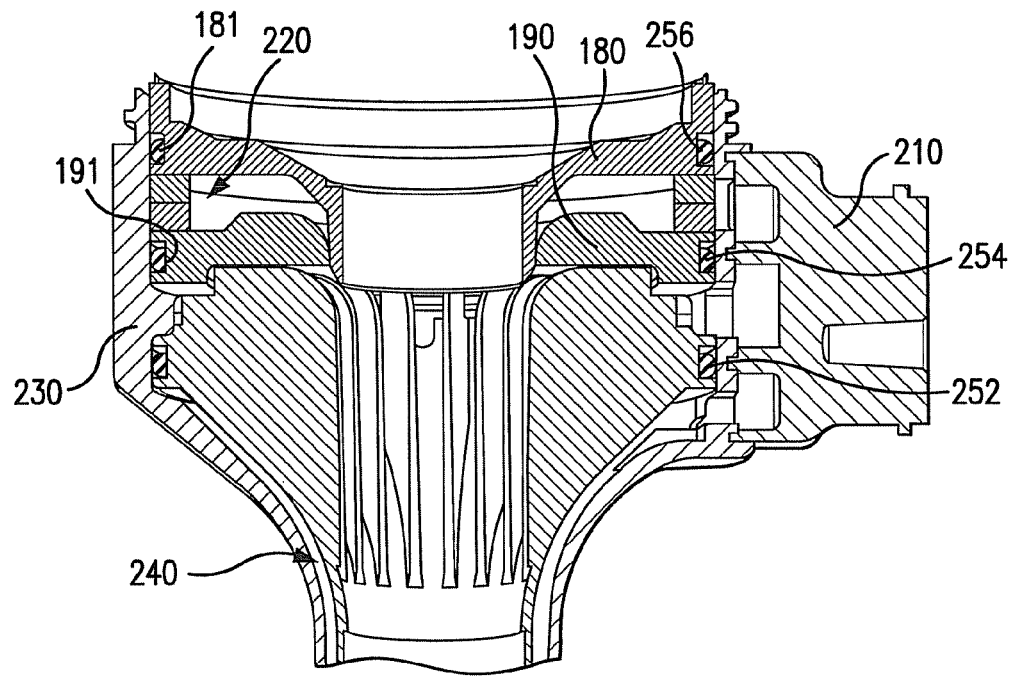
FIG. 2 is a partial view of the proximal portion of the trocar of FIG. 1, illustrating in a proximal to distal direction, the nested configuration of the tube center component, the ring jet, and the proximal vaned portion of the inner cannula seated against the inner surface of the outer cannula.
Figure 3:
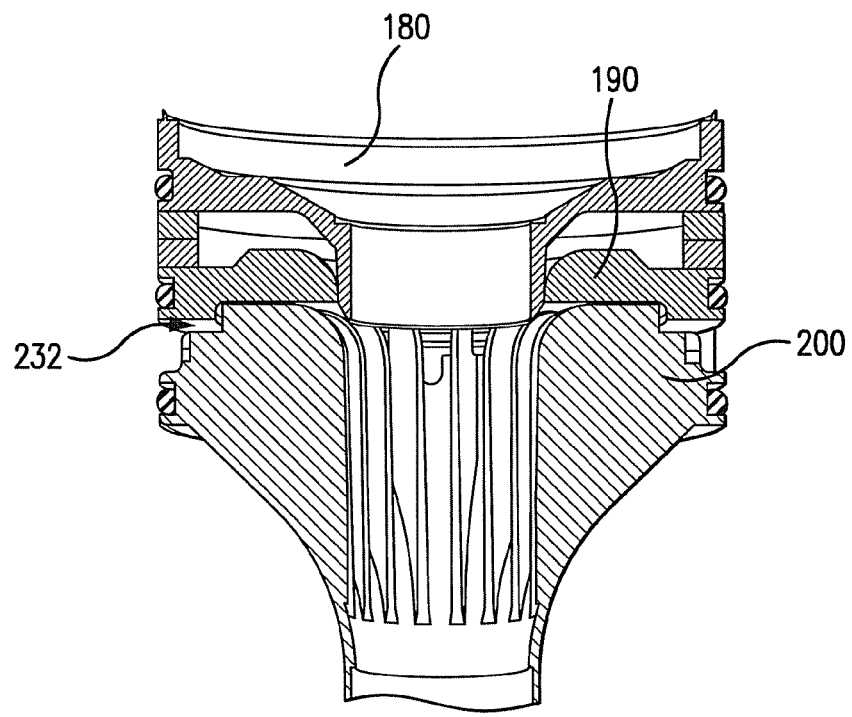
FIG. 3 is a further view identical to FIG. 2, but removing the outer cannula and associated side-mounted fluid manifold.
Figure 16:
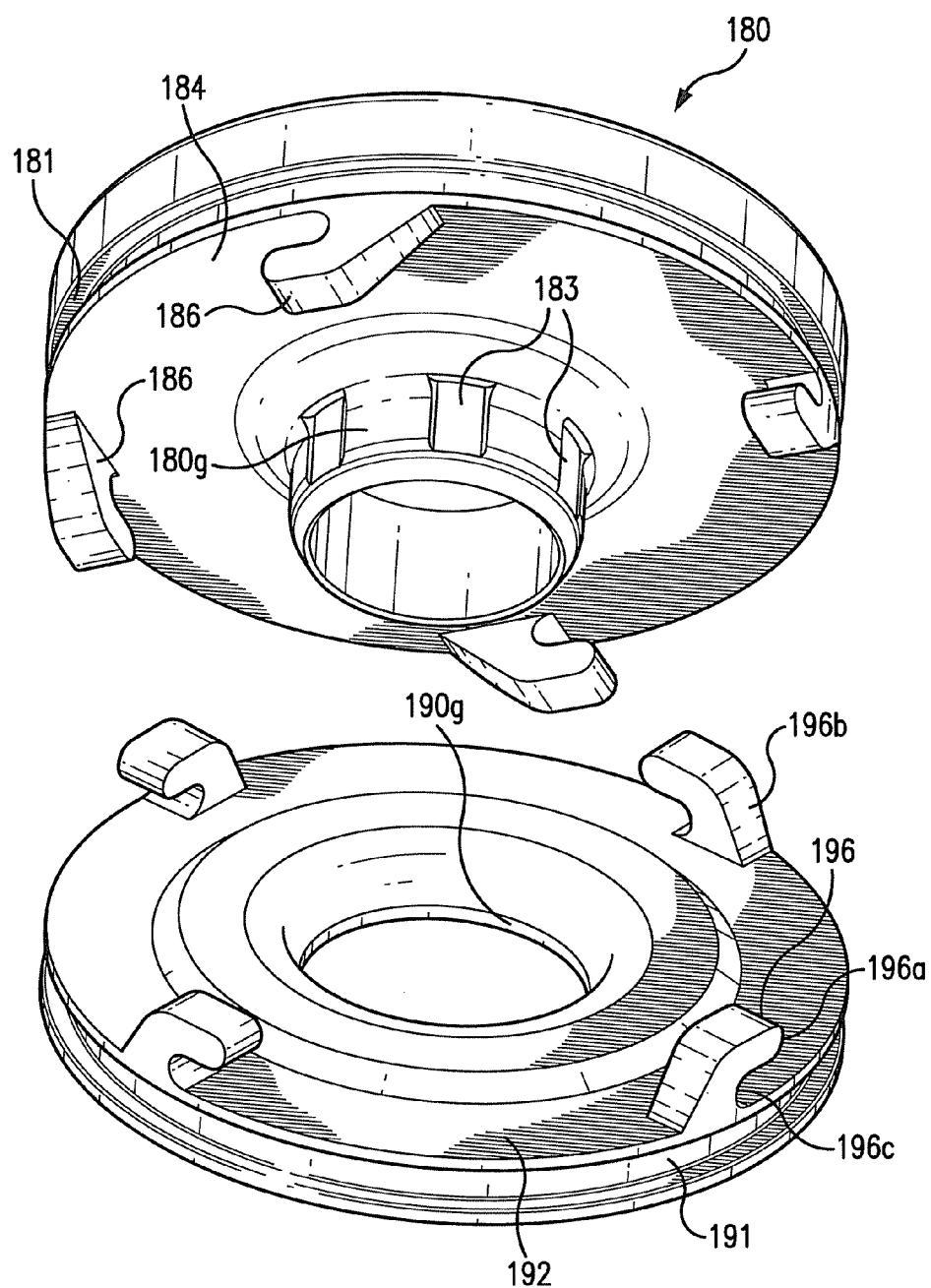
FIG. 16 is a perspective view of the tube center assembly and ring jet assembly separated from each other.
Figure 17A:
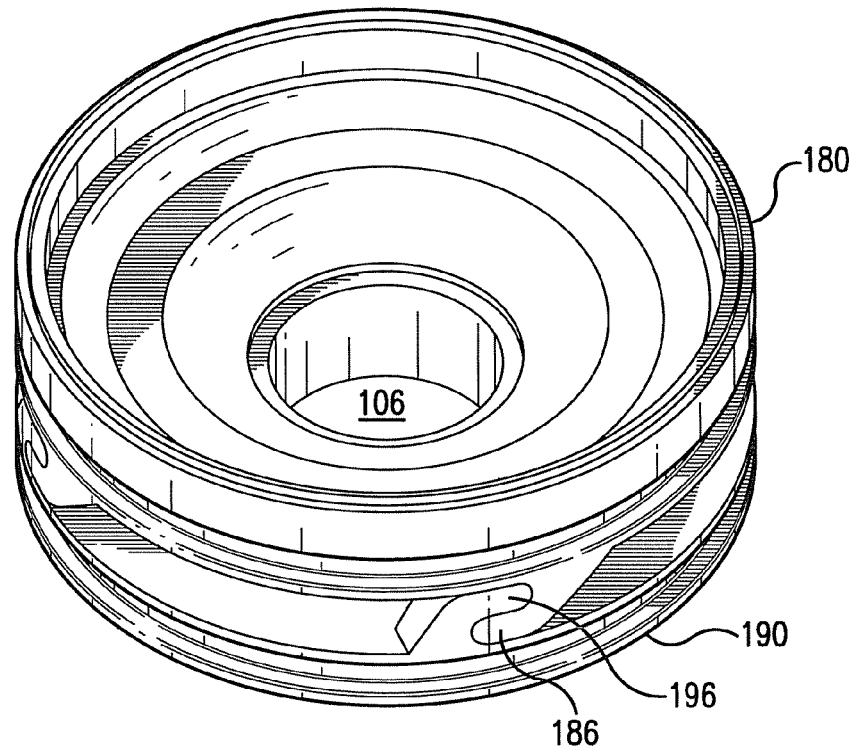
FIG. 17A is an isometric view of the tube center assembly joined to the ring jet assembly.
Figure 17B:
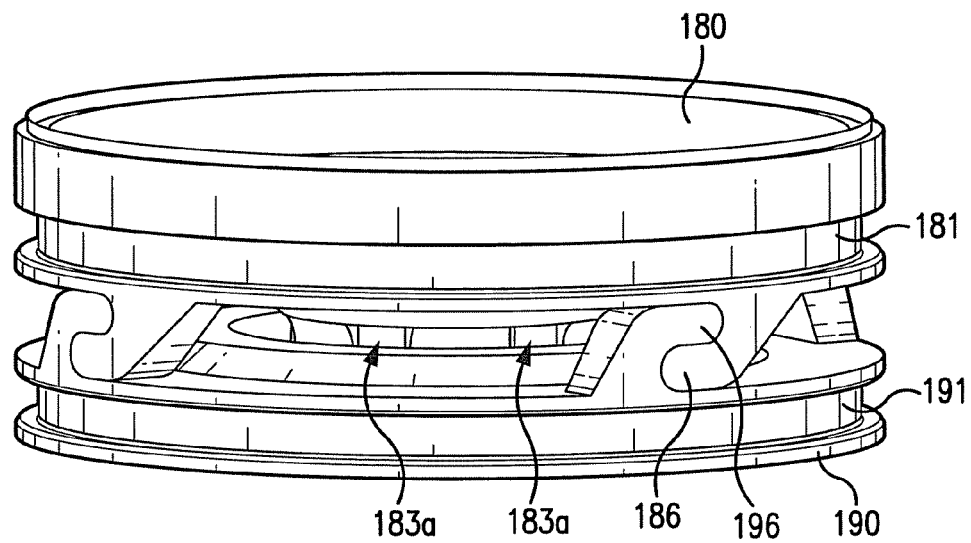
FIG. 17B is an isometric view of the tube center assembly joined to the ring jet assembly.
Figure 18:
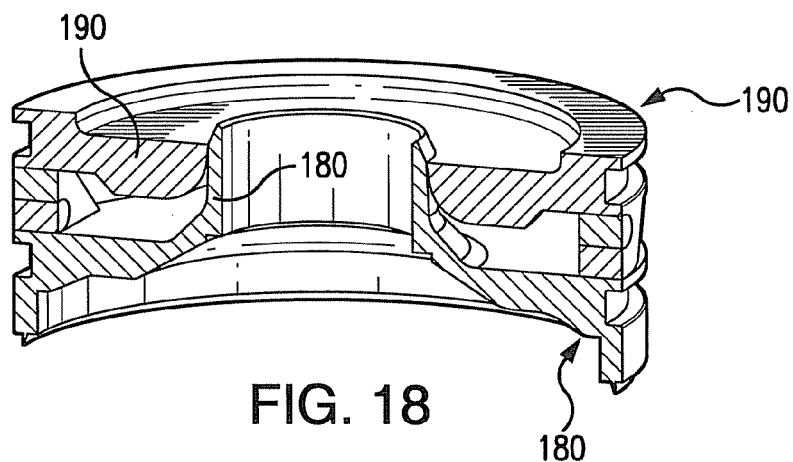
FIGS. 18 and 19 are cross-sectional views of the tube center assembly joined to the ring jet assembly taken along a plane that intersects a central longitudinal axis (herein, "longitudinal axis") of the device illustrated in FIG. 1.
Figure 19:
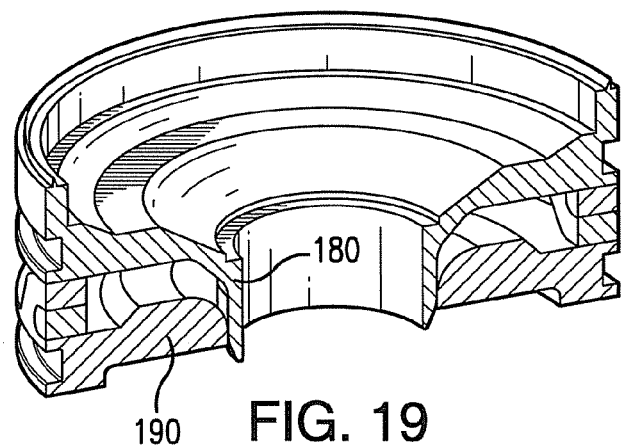
Figure 20:
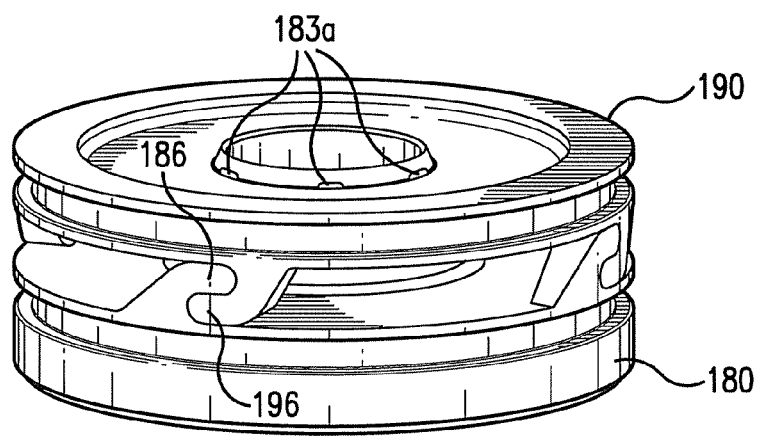
FIG. 20 is an isometric view of the tube center assembly joined to the ring jet assembly.
Figure 21D:
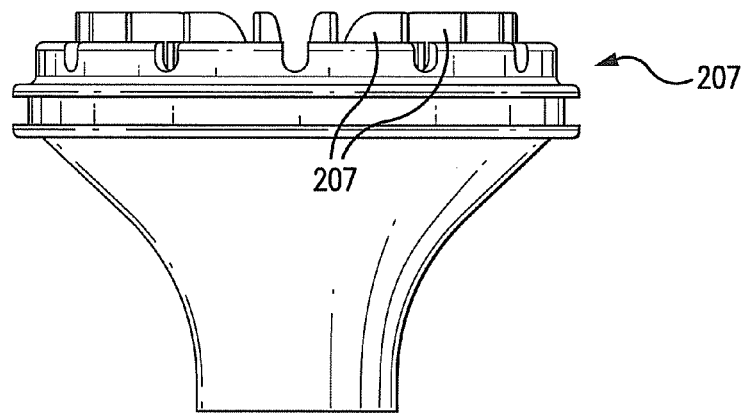
FIG. 21D is a side plan view of the proximal portion of the inner cannula.
Figure 21E:
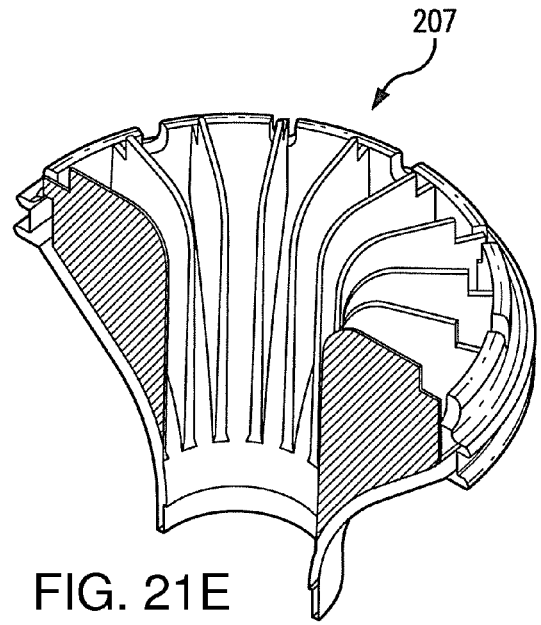
FIG. 21E is a perspective cut-away view of the proximal portion of the inner cannula.
Figure 21F:
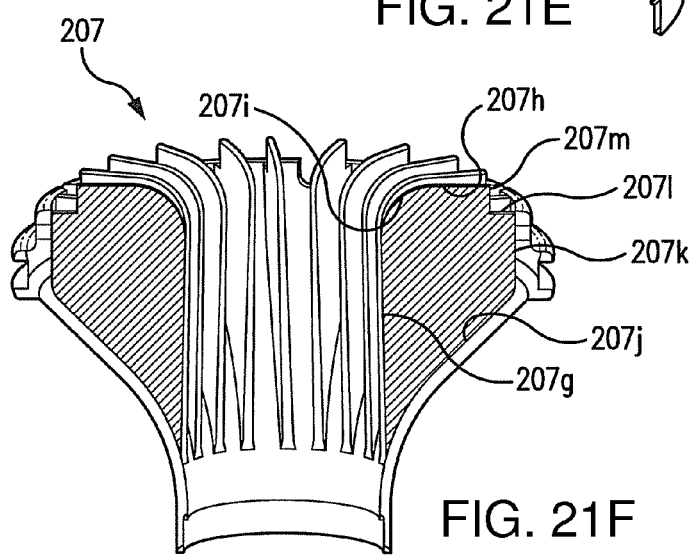
FIG. 21F is a perspective cut-away view of the proximal portion of the inner cannula.
Figure 21G:
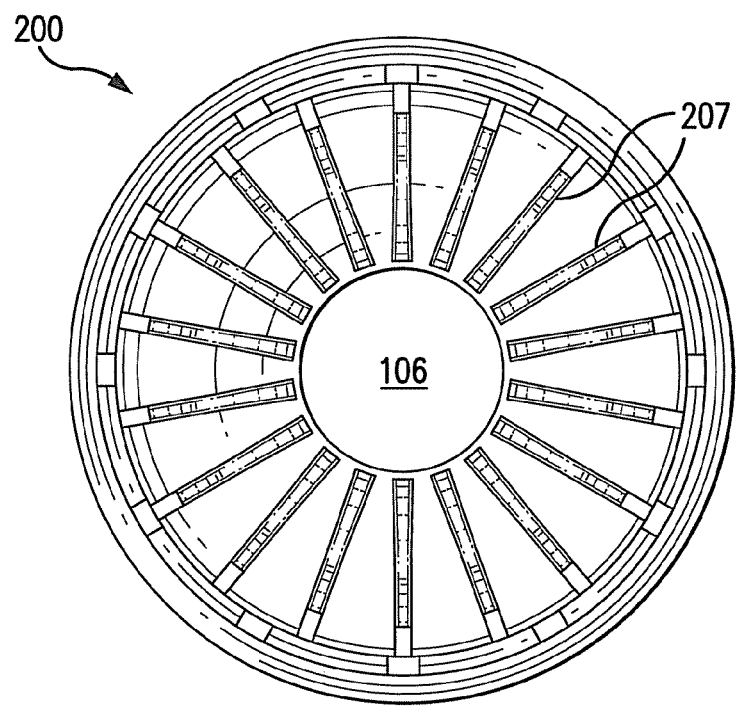
FIG. 21G is a plan proximal view of the proximal portion of the inner cannula.
Figure 21H:
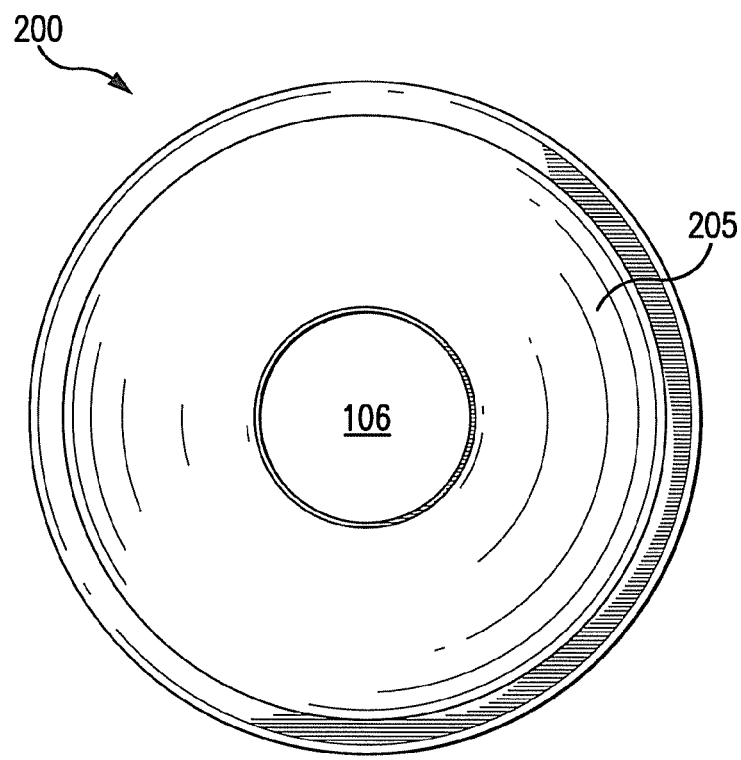
FIG. 21H is a plan distal view of the proximal portion of the inner cannula.

For purposes of further illustration, and not limitation, tube center component 180 and ring jet assembly 190 nest to form one or more fluid jets. Specifically, as illustrated in FIGS. 16-20, tube center component 180 defines one or more detents 183 on its outer surface (FIG. 16). When the outer circular surface 180g interrupted by detents 183 of center component 180 nests within the circular inner surface 190g of ring jet assembly 190, the detents 183 cooperate with the inner surface 190g of ring assembly to form a plurality of conduits, or jets, 183a (FIG. 17B) that are in fluid communication with high pressure plenum 220 (FIG. 2). It will be appreciated that any desired number and circumferential spacing of jets can be provided. High pressure plenum 220 is pressurized with a working gas so as to drive a high speed gas flow through each of the jets 183a disposed about the periphery of the distal circumferential interface of the center component 180 and the ring jet 190. As best shown in FIG. 2, a fluid tight seal about plenum 220 is ensured by seals 254, 256 disposed in circumferential grooves 181, 191 formed in each of center tube portion 180 and ring jet 190, respectively.

Preferably, the gas jets exit and wrap around the outer distal surface of the center tube component before breaking free of the surface, thus obtaining some angularity with respect to a longitudinal axis of the trocar, such that the main direction of the jet flow is generally off-axis, indicated for example by arrow "A" in FIG. 2. The momentum of the gas exiting the circumferentially disposed peripheral jets forms a stagnation point inside the bore 106 of the trocar, such that the pressure at the distal end 102 of the trocar can be about 15 mm of Hg higher than the atmospheric pressure outside the trocar in the operating room. The precise geometry of the center tube assembly 180 and the ring jet 190, and the spacing therebetween allow for a continuous stream of fluid which serves to effectively seal the lumen 106, and inhibit escape of insufflation fluid (a pneumatic seal). The lower outer circumferential edge 189 (FIG. 10A) of the tubular portion of the center tube assembly 180 is angled inward, which directs the continuous stream of fluid centrally. The fluid follows the contour of this surface 189, and is thus directed centrally, at least in part due to the Coanda effect.

With reference to FIGS. 6-20, proper axial spacing between center tube assembly 180 and ring jet 190 is ensured by the lugs 186 disposed on the distal face 184 of tube center portion 180 that interfit with lugs 196 disposed on the proximal face 192 of ring jet 190. The interfitting nature of the connection between components 180, 190 both provides a minimum spacing, but also prevents the components from separating along an axial direction of the trocar 100 caused, for example, by pressure in the trocar 100, particularly the plenum 220 (FIGS. 16-20). As best shown in FIG. 16, and using lug 196 as an example, as the ring jet defines a flat plane, each lug is illustrated as having a portion 196a that is generally parallel to that plane and a second portion 196b that is generally oblique to the plane which cooperate to define a recess 196c for receiving a complementary lug 186 on the tube center portion 180. It will be appreciated that, in addition or as an alternative to the lug connection that is illustrated, components 180, 190 can be connected by barbed tabs, ultrasonic welding, adhesive and the like. It will be further appreciated that while four connection points are provided at a radially outward portion of the periphery of the ring jet 190 and tube center portion 180, connection points can be provided in any desired number (e.g., two, three, five) and can be placed at the radial extremity as presented, and or radially inboard from that location.

As mentioned above, when assembled, the various components of trocar 100 described above cooperate to form a plurality of fluid flow paths or plena (220, 230, 240). In operation, sensing plenum 240 includes one or more pressure sensors (not shown) in a fluid flow control unit (not shown) which may be utilized to maintain the pressure of a patient's abdomen at a preselected pressure (e.g., 15 mm Hg). Suitable gas flow control units are described, for example, in Provisional Patent Application Ser. No. 61/246,921, which is incorporated by reference herein in its entirety. For example, if the pressure detected in the abdomen is too high, the flow control unit decreases the delivery of gas to plenum 220, resulting in less gas being delivered through the high speed jets and into the bore 106 of the trocar 100. By way of further example, if the gas pressure is too low in the abdomen, the flow control unit increases the delivery of gas to plenum 220, resulting in more gas being delivered through the high speed jets and into the bore 106 of the trocar 100.

With reference now to FIGS. 2-5 and 21A-21H, portion 200 of inner cannula 120 preferably defines a peripheral groove 211 about the proximal end 202 thereof that is adapted and configured to receive a deformable sealing ring 252, such as an o-ring (see FIG. 2). When assembled, sealing ring 252 is interposed between outer cannula 110 and inner cannula 120, thereby defining sensing plenum 240 in cooperation with dedicated passageway in manifold 210.

Figure 4:
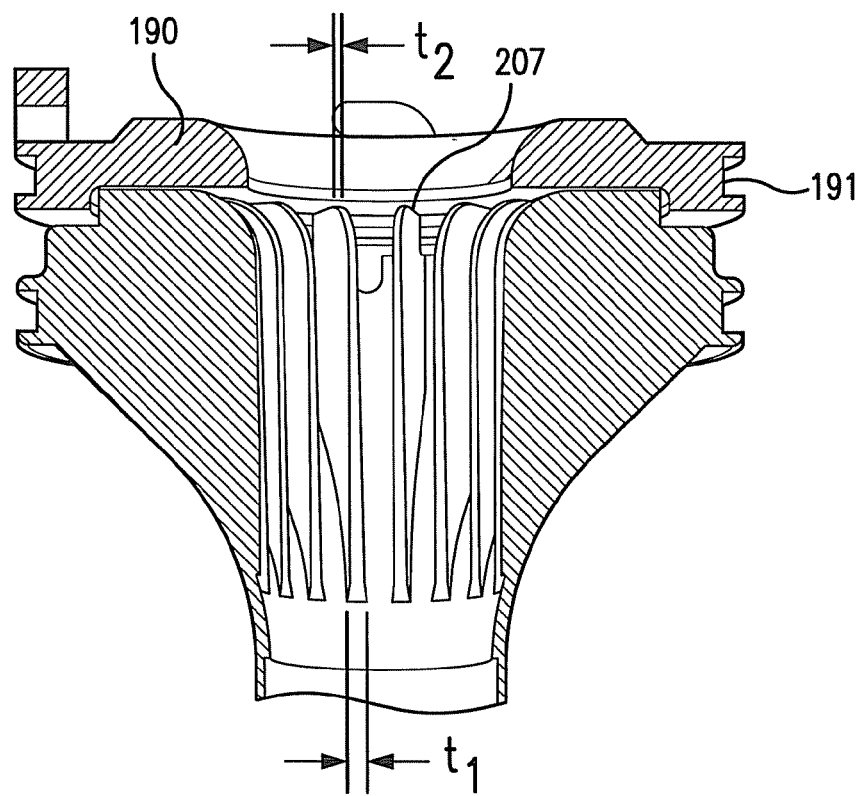
FIG. 4 is a further view identical to FIG. 3, but removing the tube center component and exemplary o-ring seals.
Figure 5:
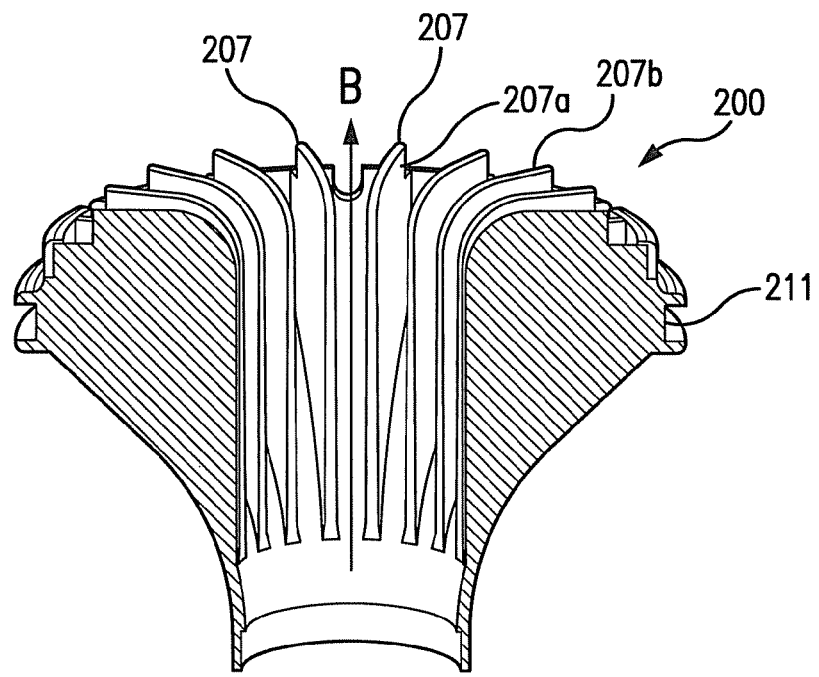
FIG. 5 is a further view identical to FIG. 4, but removing the ring jet and leaving a view of the proximal portion of the inner cannula.
Figure 6:
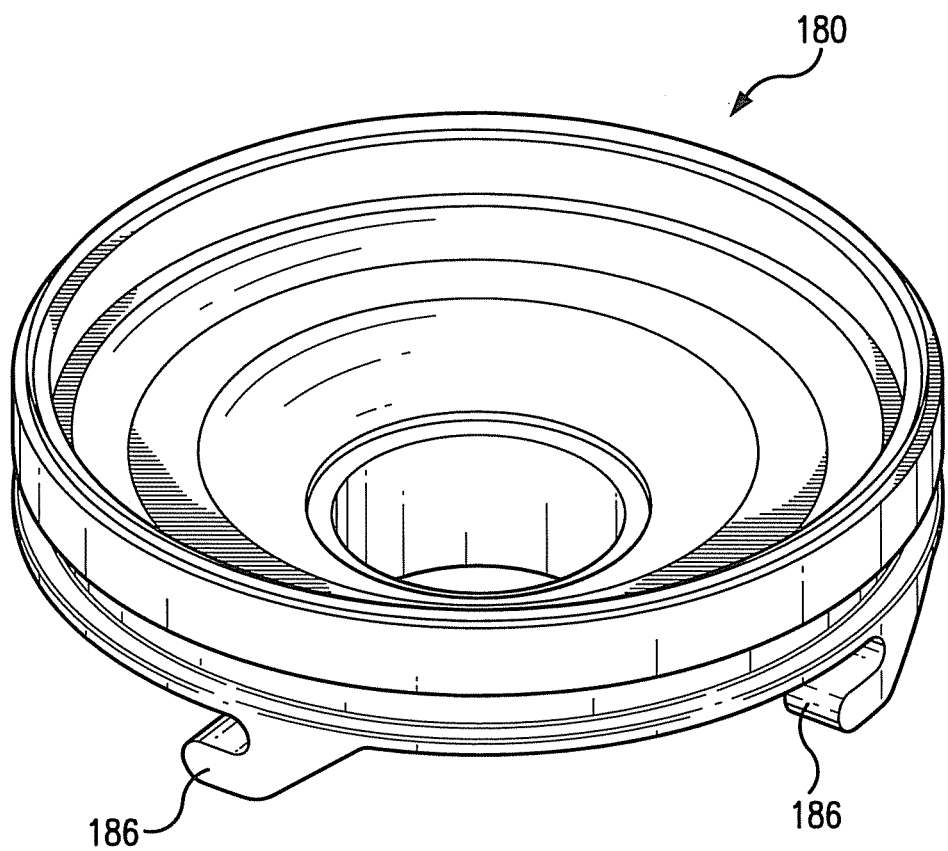
FIG. 6 is a perspective top/proximal view of the tube center assembly.
Figure 7:
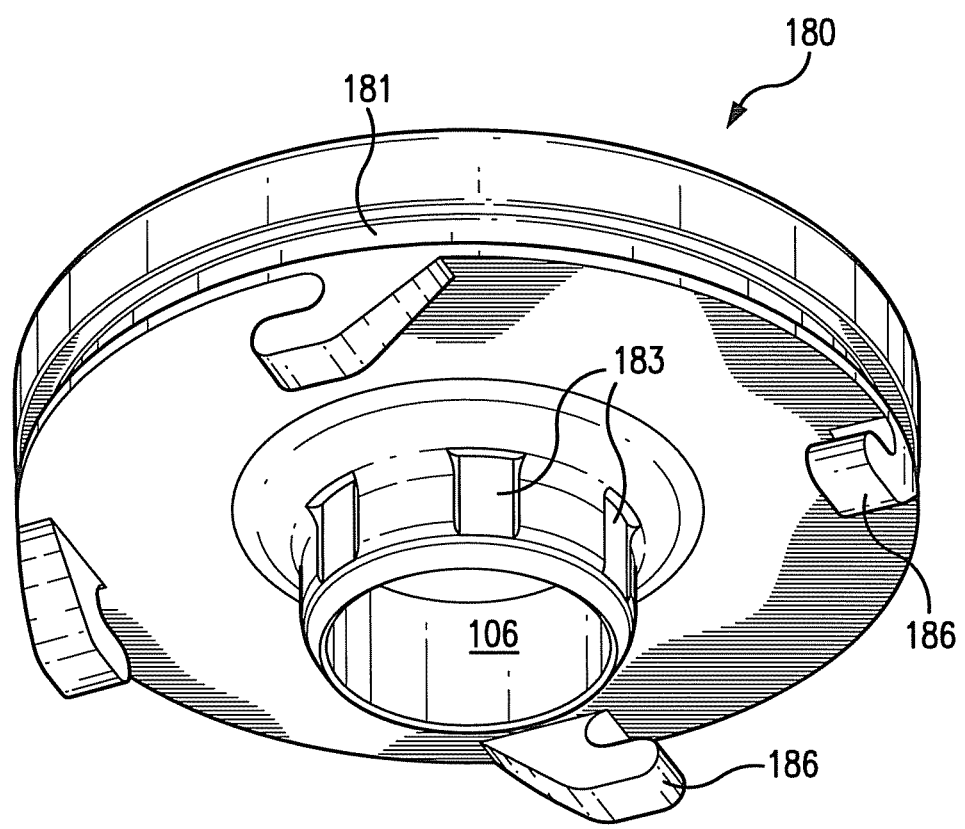
FIG. 7 is a perspective bottom/distal view of the tube center assembly.
Figure 8:
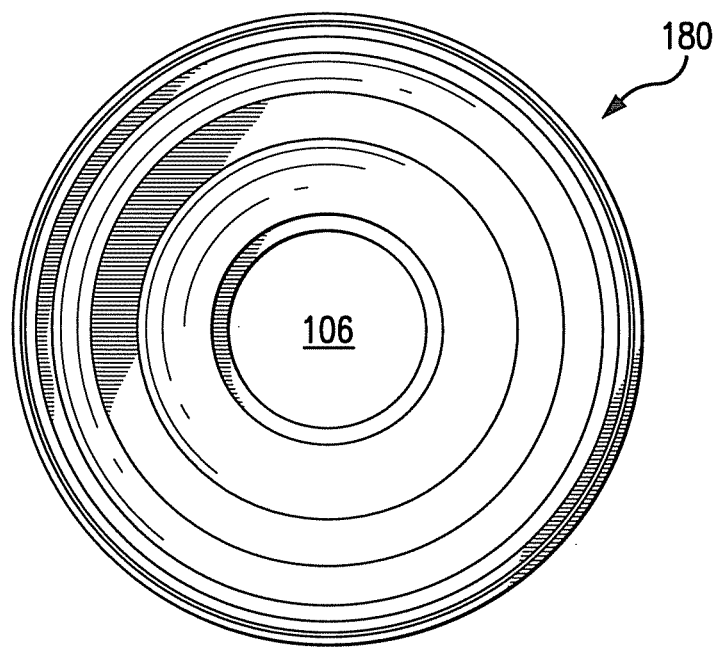
FIG. 8 is a plan top/proximal view of the tube center assembly.
Figure 9:
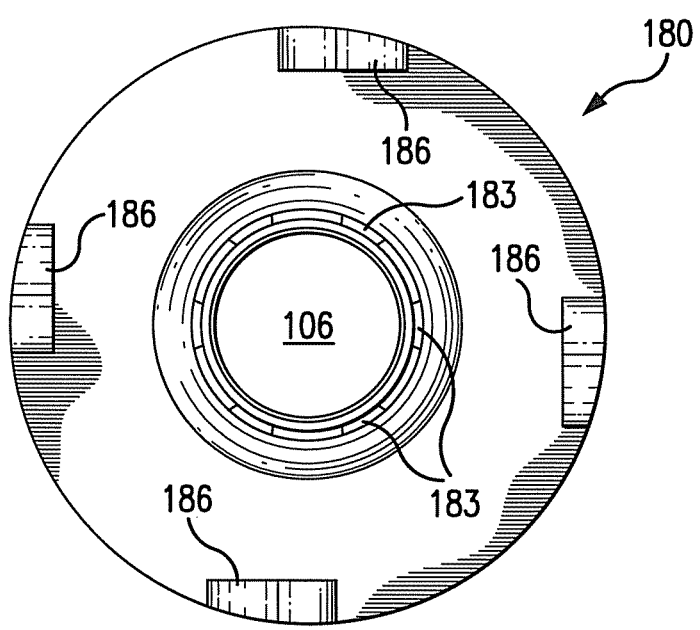
FIG. 9 is a plan bottom/distal view of the tube center assembly.
Figure 10A:
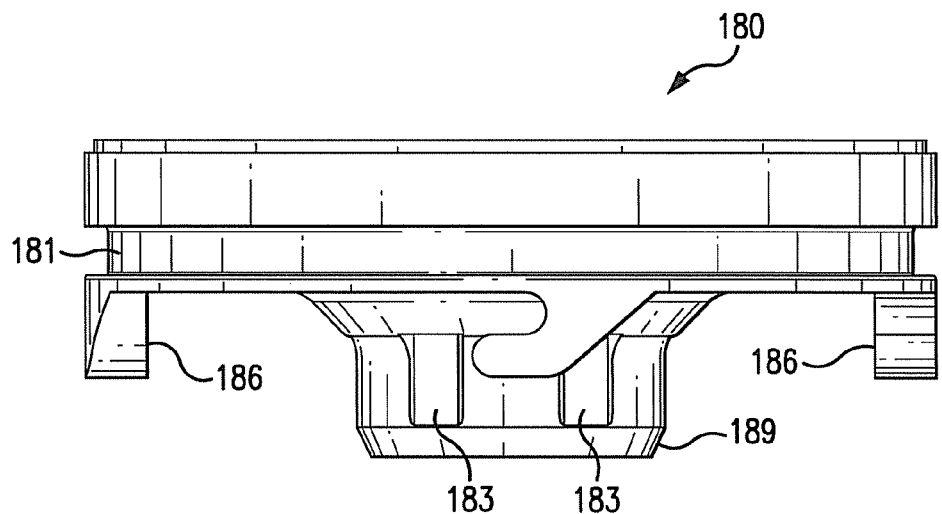
FIG. 10A is a side view of the tube center assembly.
Figure 10B:
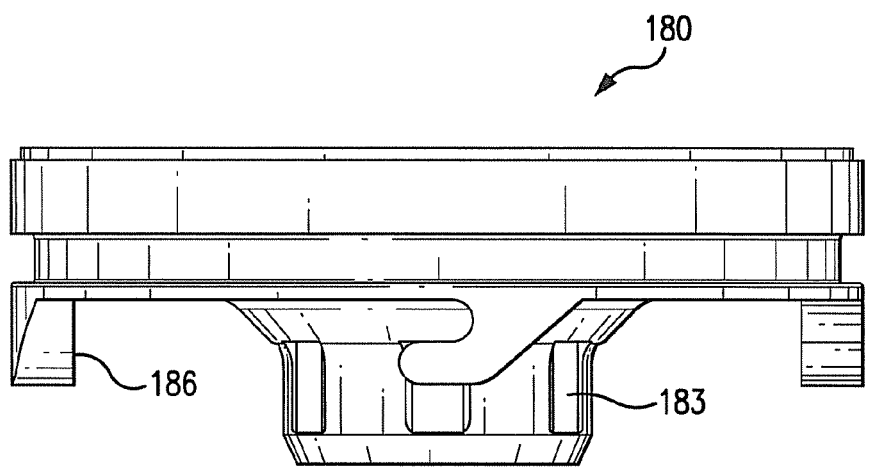
Figure 11:
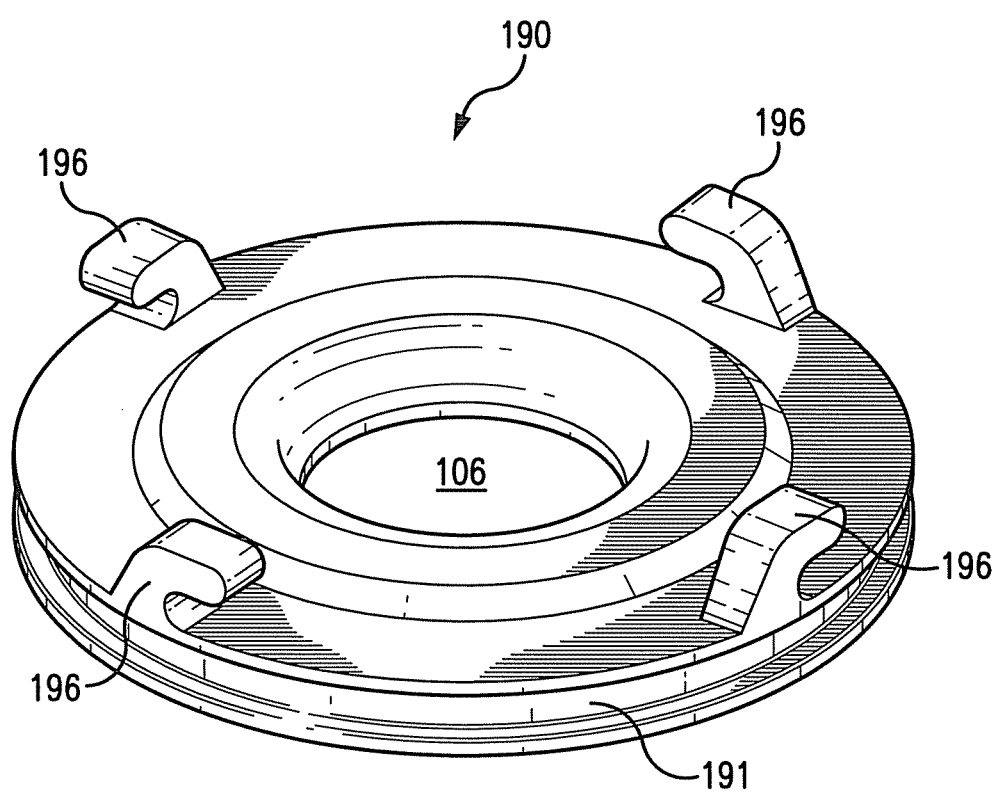
FIG. 11 is a perspective top/proximal view of the ring jet assembly.

Vaned portion 200 of inner cannula 120 is defined by a conical outer sleeve 205 having a concave hyperbolic shape and a plurality of axially and radially oriented vanes 207 that extend from a point proximal to the proximal end of the outer sleeve 205 to a point just proximal of the distal end of the outer sleeve 205. As illustrated in FIG. 4, each vane 207 has a thickness t1 at its distal portion that gradually decreases along the length of the vane to its proximal end having a thickness t2. As further disclosed in FIG. 21F, each vane includes an edge 207g that is substantially parallel to a longitudinal axis of the device 100 joined to a proximal edge 207h that is perpendicular to the longitudinal axis of the device 100 by a curved segment 207i. The profile of vane 207 is further comprised of an outer edge 207j having a hyperbolic shape joined to a further edge 207k that is parallel to the axis of the device 100 and constitutes a radial outward edge, which is in turn joined to a further edge 207l which is perpendicular to the longitudinal axis of the device 100. Edge 207l is joined to edge 207m, which is parallel to the longitudinal axis of the device and is joined to portion 207h. As is evident, eighteen vanes 207 are present in the illustrated embodiment, but any number can be used, as desired. Each pair of vanes 207 defines a flow channel 207a therebetween (FIG. 5) to permit flow to proceed between the vanes along direction B (FIG. 5) to direct recirculated gas back to the recirculation plenum 230, and to prevent interference with flow emanating from jets 183 discussed above. Preferably, each vane 207 is adapted and configured to also provide sound attenuation with respect to the sound emitted from the spent insufflation fluid flowing through the trocar 100.

Figure 12:
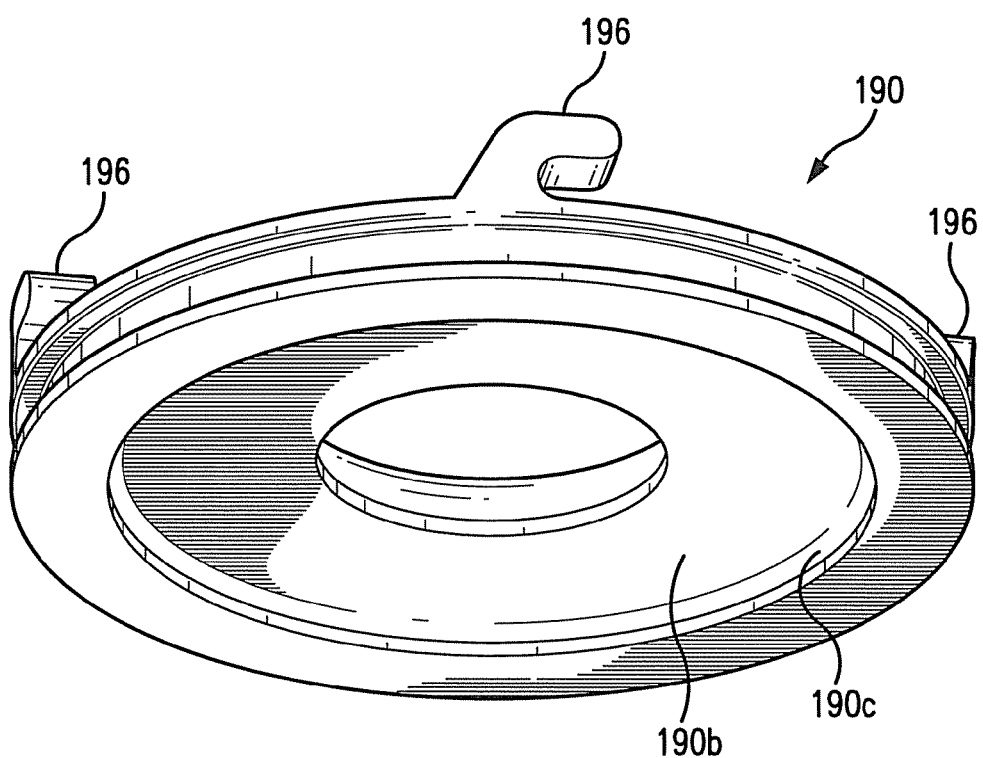
FIG. 12 is a perspective bottom/distal view of the ring jet assembly.
Figure 13:
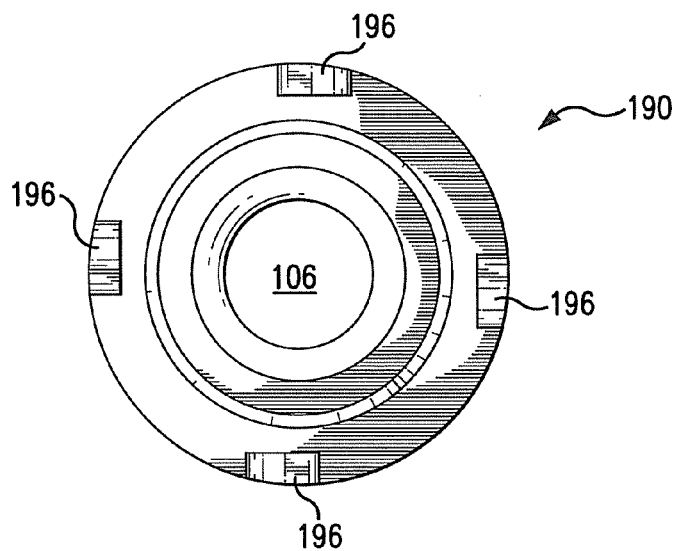
FIG. 13 is a plan top/proximal view of the ring jet assembly.
Figure 14:
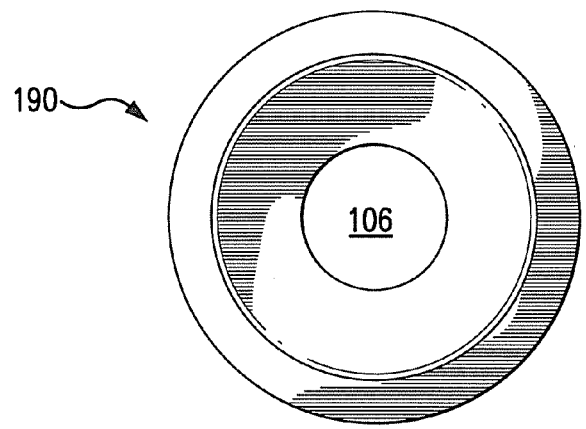
FIG. 14 is a plan bottom/distal view of the ring jet assembly.
Figure 15:
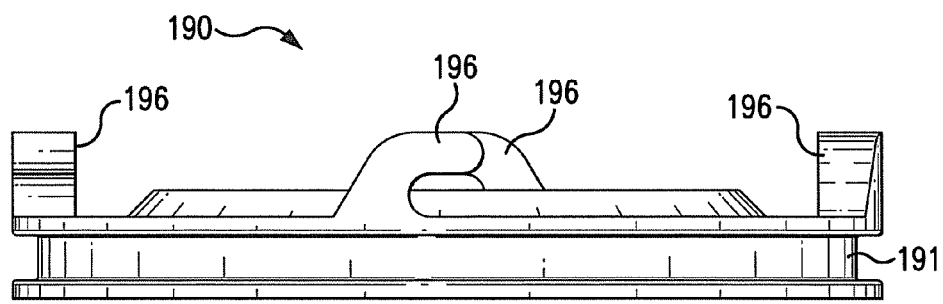
FIG. 15 is a side view of the ring jet assembly.

Proximal circumferential periphery 202 of portion 200 further defines a series of arcuate notches 223 along the upper periphery thereof (FIGS. 21B, 21C). The proximal surfaces 207b of vanes 207 seat against circular surface 190b of ring jet 190 that is bounded by a circular peripheral wall 190c (FIG. 12). When assembled, ring jet 190 and portion 200 cooperate to define a peripheral annular gap 232a between the two components, which, in combination with notches 223 act as a fluid passage in fluid communication with passage 232 to define an exhaust or recirculation plenum 230, described in further detail below, for evacuating gas and other fluids from trocar 100 and/or the abdomen of the patient into a filtration and recirculation assembly (not shown).

The methods and systems of the present disclosure, as described above and shown in the drawings, provide for trocars and surgical systems with superior attributes as compared with systems of the prior art. It will be apparent to those skilled in the art that various modifications and variations can be made in the device and method of the present disclosure without departing from the spirit or scope of the disclosure. Thus, it is intended that the present disclosure include modifications and variations that are within the scope of the subject disclosure and equivalents.

What is claimed is:

1. A nozzle assembly for generating a gaseous seal, comprising:
   a) an upper nozzle portion including an annular body having an outer periphery and an inner periphery, the inner periphery defining a downwardly extending nozzle tube having a radially outer surface, wherein the radially outer surface of the nozzle tube includes a plurality of circumferentially spaced apart recessed surface areas defining a plurality of circumferentially spaced apart raised surface areas;
   b) a lower nozzle portion including an annular body having an outer periphery and an inner periphery, the inner periphery defining a beveled surface area configured for intimate engagement with the plurality of circumferentially spaced apart raised surface areas of the nozzle tube, whereby the spaced apart recessed surface areas of the nozzle tube and the beveled surface area form a ring of circumferentially spaced apart jets for generating a gaseous seal; and
   c) a locking assembly cooperatively associated with the outer periphery of the upper and lower nozzle portions for interlocking the nozzle portions together and maintaining a minimum axial spacing therebetween to form a high pressure interior plenum that communicates with the ring of circumferentially spaced apart jets, wherein the locking assembly includes a plurality of circumferentially spaced apart interfitting engagement lugs that define a plurality of circumferentially spaced apart passages in an outer periphery of the nozzle assembly that communicate with the high pressure interior plenum.

2. A nozzle assembly as recited in claim 1, wherein the lugs include a first set of lugs that extend downwardly from an outer periphery of the upper nozzle portion.

3. A nozzle assembly as recited in claim 2, wherein the lugs further include a second set of lugs that extend upwardly from an outer periphery of the lower nozzle portion.

4. A nozzle assembly as recited in claim 1, wherein the nozzle tube has a radially inwardly tapering lower outer circumferential edge for directing gas exiting the ring of circumferentially spaced apart jets radially inwardly.

5. A nozzle assembly as recited in claim 1, wherein the outer periphery of the upper and lower nozzle portion each include an annular groove for accommodating a seal.

6. A nozzle assembly for generating a gaseous seal, comprising:
   a) an upper nozzle portion including an annular body having an outer periphery and an inner periphery, the outer periphery including a plurality of circumferentially spaced apart downwardly extending upper engagement lugs, the inner periphery defining a downwardly extending nozzle tube having a radially outer surface, wherein the radially outer surface of the nozzle tube includes a plurality of circumferentially spaced apart recessed surface areas defining a plurality of circumferentially spaced apart raised surface areas; and
   b) a lower nozzle portion including an annular body having an outer periphery and an inner periphery, the outer periphery including a plurality of circumferentially spaced apart upwardly extending lower engagement lugs configured to interfit with the upper engagement lugs of the upper nozzle portion, the inner periphery defining a beveled surface area configured for intimate engagement with the plurality of circumferentially spaced apart raised surface areas of the nozzle tube, whereby the spaced apart recessed surface areas of the nozzle tube and the beveled surface area form a ring of circumferentially spaced apart jets for generating a gaseous seal, and wherein the plurality of circumferentially spaced apart interfitting engagement lugs are configured to maintain the upper and lower nozzle portions of the nozzle assembly in an axial spaced relationship so as to form a high pressure interior plenum therebetween that communicates with the ring of spaced apart jets and further define a plurality of circumferentially spaced apart passages in an outer periphery of the nozzle assembly that communicate with the high pressure interior plenum.

7. A nozzle assembly as recited in claim 6, wherein the nozzle tube has a radially inwardly tapering lower outer circumferential edge for directing gas exiting the ring of circumferentially spaced apart jets radially inwardly.

8. A nozzle assembly as recited in claim 6, wherein the outer periphery of the upper and lower nozzle portion each includes an annular groove for accommodating a seal.

\* \* \* \* \*